§ 371 (c)(1),
(12) United States Patent
Sera et al.

(10) Patent No.: US 9,095,159 B2
(45) Date of Patent: Aug. 4, 2015

(54) COMPOSITION CONTAINING BACTERIUM CAPABLE OF PRODUCING PROPIONIC ACID BACTERIUM, AND USE THEREOF

(75) Inventors: Kenji Sera, Saitama (JP); Katsunori Kimura, Odawara (JP); Michio Kanbe, Higashimurayama (JP); Takenori Orihashi, Fuchu (JP); Manami Yoshida, Mito (JP); Yoshiaki Obara, Ryuugasaki (JP)

(73) Assignees: MEIJI FEED Co., Ltd., Tokyo (JP); Meiji Co., Ltd., Tokyo (JP)

( * ) Notice: Subject to any disclaimer, the term of this patent is extended or adjusted under 35 U.S.C. 154(b) by 0 days.

(21) Appl. No.: 13/518,544

(22) PCT Filed: Dec. 22, 2010

(86) PCT No.: PCT/JP2010/073111
(2), (4) Date: Jul. 23, 2012

(87) PCT Pub. No.: WO2011/078213
PCT Pub. Date: Jun. 30, 2011

(65) Prior Publication Data
US 2012/0276055 A1    Nov. 1, 2012

(30) Foreign Application Priority Data

Dec. 25, 2009  (JP) ................. 2009-295811

(51) Int. Cl.
*A61K 35/74* (2006.01)
*A61P 1/04* (2006.01)
*C12N 1/20* (2006.01)
*A23K 1/18* (2006.01)
*A23K 1/00* (2006.01)
*A61K 35/741* (2015.01)

(52) U.S. Cl.
CPC ............... *A23K 1/1813* (2013.01); *A23K 1/009* (2013.01); *A61K 35/741* (2013.01)

(58) Field of Classification Search
None
See application file for complete search history.

(56) References Cited

U.S. PATENT DOCUMENTS 5,534,271 A  *  7/1996  Ware et al. ................... 426/2
7,063,836 B2 *  6/2006  Garner et al. ............. 424/93.45

OTHER PUBLICATIONS

Heinrichs, AJ; et al; "Effects of a prebiotic supplement on health of neonatal dairy calves" Livestock Science, 125, 149-154, 2009.*
Fujisawa, Tomohiko; et al; "Influences of Prebio Support™ (Mixture of Fermented Products of *Lactobacillus gasseri* OLL2716 and *Propionibacterium freudenreichii* ET-3) on the Composition and Metabolic Activity of Fecal Microbiota in Calves" Bioscience Microflora, 29, 41-45, 2010.*
Olmstead, Stephen; et al; "Making Sense of Probiotics" Klaire Labs Newsletter, Technical Summary, 2003.*
Parrott, TD; et al; "Selection of *Propionbacterium* Strains Capable of Utilizing Lactic Acid from In Vitro Models" Joint Meeting of ADSA, AMSA, ASAS and PSA, Indianapolis, 39-50, 2001.*
International Search Report issued on Apr. 5, 2011 in PCT/JP10/073111 filed on Dec. 25. 2010.

* cited by examiner

*Primary Examiner* — Blaine Lankford
*Assistant Examiner* — David Berke-Schlessel
(74) *Attorney, Agent, or Firm* — Oblon, McClelland, Maier & Neustadt, L.L.P.

(57) ABSTRACT

The invention provides a composition that enhances the proliferation activity of propionic acid bacteria in the rumen of ruminants to allow the propionic acid bacteria to sufficiently exhibit their metabolic function in the rumen for the prevention and treatment of rumen acidosis in ruminants. The invention also provides use of the composition. Viable propionic acid bacteria and a lactic acid bacteria culture are orally administered to a ruminant to dramatically (rapidly) promote the proliferation of the propionic acid bacteria in the ruminant rumen, and to thereby increase the volatile fatty acid concentration in the rumen for the prevention and/or treatment of rumen acidosis in the ruminant.

7 Claims, 2 Drawing Sheets

COMPOSITION CONTAINING BACTERIUM CAPABLE OF PRODUCING PROPIONIC ACID BACTERIUM, AND USE THEREOF

This application is a National Stage of PCT/JP10/073,111 filed Dec. 22, 2010 and claims the benefit of JP 2009-295811 filed Dec. 25, 2009.

TECHNICAL FIELD

The present invention relates to methods and compositions for preventing and treating rumen acidosis in ruminants. Specifically, the invention relates to methods and compositions for suppressing an overincrease of lactic acid in the rumen of ruminants for the prevention and treatment of rumen acidosis in ruminants.

BACKGROUND ART

In ruminants (for example, cows), seventy percent of the energy needed to maintain the body comes from the volatile fatty acids (VFAs) produced in the rumen (first chamber). The main VFAs produced by rumen fermentation are acetic acid, propionic acid, and butyric acid, of which the propionic acid has the highest energy efficiency. For example, in the rumen of cows, propionic acid is synthesized by rumen fermentation from materials such as fibers, some sugars, and starches, which are converted into glucose in the liver, and used as the energy source, and as the raw material for producing milk and meat.

The rumen environment of ruminants is strongly influenced by feeds and other factors, and accordingly the rumen fermentation greatly fluctuates according to these factors. For the purpose of improving the productivity of domestic animals, there has been a practice of feeding grains and other concentrated feeds in large quantity. However, this often leads to crude fiber deficiency, and the excess supply of easily fermentable carbohydrates. All this causes disturbances in rumen homeostasis, and various metabolic defects (known as production disease).

For example, a marked increase in lactic acid resulting from the proliferation of lactic acid bacteria such as *Lactobacillus* and *Streptococcus bovis* under a large supply of concentrated feeds and under crude fiber deficient conditions brings the rumen pH to 5 or less (from the normal pH of 6 to 7), and causes acute acidosis (a state referred to as rumen acidosis). Symptoms of rumen acidosis in cows include a rapid decrease in feeding levels, a decrease in the percentage of milk fat, loose stool, strong acid odor, and high incidence of claudication. The result is lowered production efficiency such as in milk production.

Although no prominent clinical presentation is seen at the site of production, great many cases of latent acidosis are suspected in domestic ruminants, which raises concerns that latent acidosis, in fact, has large impact on production efficiency such as in milk production. An important challenge, therefore, is to develop a technique for controlling rumen fermentation.

Under these circumstances, there have been proposed methods of administering propionic acid bacteria for the purpose of improving the activity of lactic acid bacteria, and thus improving the enteral environment (Patent Documents 1 and 2). However, activating only the lactic acid bacteria might instead increase the lactic acid in the rumen, and promote acidosis. Further, there have been attempts to directly administer viable propionic acid bacteria to ruminants to activate the propionic acid bacteria present in the rumen. However, the propionic acid bacteria are very difficult to proliferate, and the level of propionic acid bacteria in the rumen greatly fluctuates and becomes unstable depending on such factors as the type of feed. It is therefore difficult to sufficiently improve the rumen activity merely by supplementing propionic acid bacteria in the rumen.

PRIOR ART DOCUMENTS

Patent Documents

Patent Document 1: JP-A-2006-254841
Patent Document 2: JP-A-2000-256201

SUMMARY OF THE INVENTION

Problem to be Solved by the Invention

The present invention has been made under the foregoing circumstances, and it is an object of the present invention to provide a composition for preventing and treating rumen acidosis in ruminants by enhancing the proliferation activity of propionic acid bacteria in the rumen, and by thus allowing the propionic acid bacteria in the ruminant rumen to sufficiently exhibit its metabolic function. The invention also provides use of the composition. A secondary object of the present invention is to improve the quality and productivity of milk and meat in domestic ruminants, which is achieved by increasing the concentration of volatile fatty acids such as propionic acid in the rumen through the metabolic function of propionic acid bacteria.

Means for Solving Problem

In order to achieve the foregoing objects, the present inventors conducted a wide range of studies, and found that oral administration of viable propionic acid bacteria and a lactic acid bacteria culture to the ruminants dramatically (rapidly) promotes proliferation of propionic acid bacteria in the ruminant rumen, and rapidly increases the propionic acid bacteria and activates rumen fermentation to increase the volatile fatty acid concentration in the rumen, and thus enables prevention and/or treatment of rumen acidosis in ruminants. The present invention was completed based on these findings.

Specifically, the present invention is embodied as follows.

(1) A method for promoting proliferation of propionic acid bacteria,
the method comprising adding a viable propionic acid bacterium and a lactic acid bacteria culture.

(2) A method for preventing and/or treating rumen acidosis in ruminants,
the method comprising orally administering a viable propionic acid bacterium and a lactic acid bacteria culture (here and below, the lactic acid bacteria culture includes viable and/or killed lactic acid bacteria) to a ruminant.

(3) A method for (rapidly) promoting proliferation of propionic acid bacteria in the rumen of ruminants,
the method comprising orally administering a viable propionic acid bacterium and a lactic acid bacteria culture to a ruminant.

(4) A method for increasing the volatile fatty acid concentration in the rumen of ruminants,
the method comprising orally administering a viable propionic acid bacterium and a lactic acid bacteria culture to a ruminant.

(5) The method according to any one of (1) to (4), wherein the propionic acid bacterium is *Propionibacterium freudenreichii*.

(6) The method according to any one of (1) to (5), wherein the lactic acid bacteria culture is a *Lactobacillus gasseri* culture.

(7) The method according to (5) or (6), wherein the propionic acid bacterium is the *Propionibacterium freudenreichii* ET-3 strain (FERM BP-8115), and wherein the lactic acid bacteria culture is a culture of the *Lactobacillus gasseri* OLL2716 strain (FERM BP-6999).

(8) The method according to any one of (2) to (7), wherein the ruminant is a cow.

(9) A composition for preventing and/or treating rumen acidosis in ruminants, wherein the composition comprises a viable propionic acid bacterium and a lactic acid bacteria culture as active ingredients (an agent, or a feed for ruminants as a ruminant drug for preventing and/or treating rumen acidosis).

(10) The composition according to (9), wherein the propionic acid bacterium is *Propionibacterium freudenreichii*.

(11) The composition according to (9) or (10), wherein the lactic acid bacteria culture is a *Lactobacillus gasseri* culture.

(12) The composition according to (10) or (11), wherein the propionic acid bacterium is the *Propionibacterium freudenreichii* ET-3 strain (FERM BP-8115), and wherein the lactic acid bacteria culture is a culture of the *Lactobacillus gasseri* OLL2716 strain (FERM BP-6999).

(13) The composition according to any one of (9) to (12), wherein the ruminant is a cow.

(14) An agent for promoting proliferation of propionic acid bacteria, wherein the agent comprises a viable propionic acid bacterium and a lactic acid bacteria culture as active ingredients (for both medicinal applications and food applications).

Effect of the Invention

In the present invention, two active ingredients, viable propionic acid bacteria and a lactic acid bacteria culture, are orally administered to a ruminant to enhance the proliferation activity of not only the administered propionic acid bacteria but the propionic acid bacterium residing in the rumen. This rapidly promotes the proliferation of the propionic acid bacteria in the rumen, and highly activates (promotes) rumen fermentation such as the conversion of lactic acid into propionic acid by the propionic acid bacteria. In this way, the rumen acidosis (including latent acidosis) caused by an over-increase of lactic acid in the rumen of ruminants can be prevented and treated. Further, the quality and productivity of milk and meat in domestic ruminants can be improved by the increased levels of volatile fatty acids such as propionic acid.

MODE FOR CARRYING OUT THE INVENTION

Figure 1:
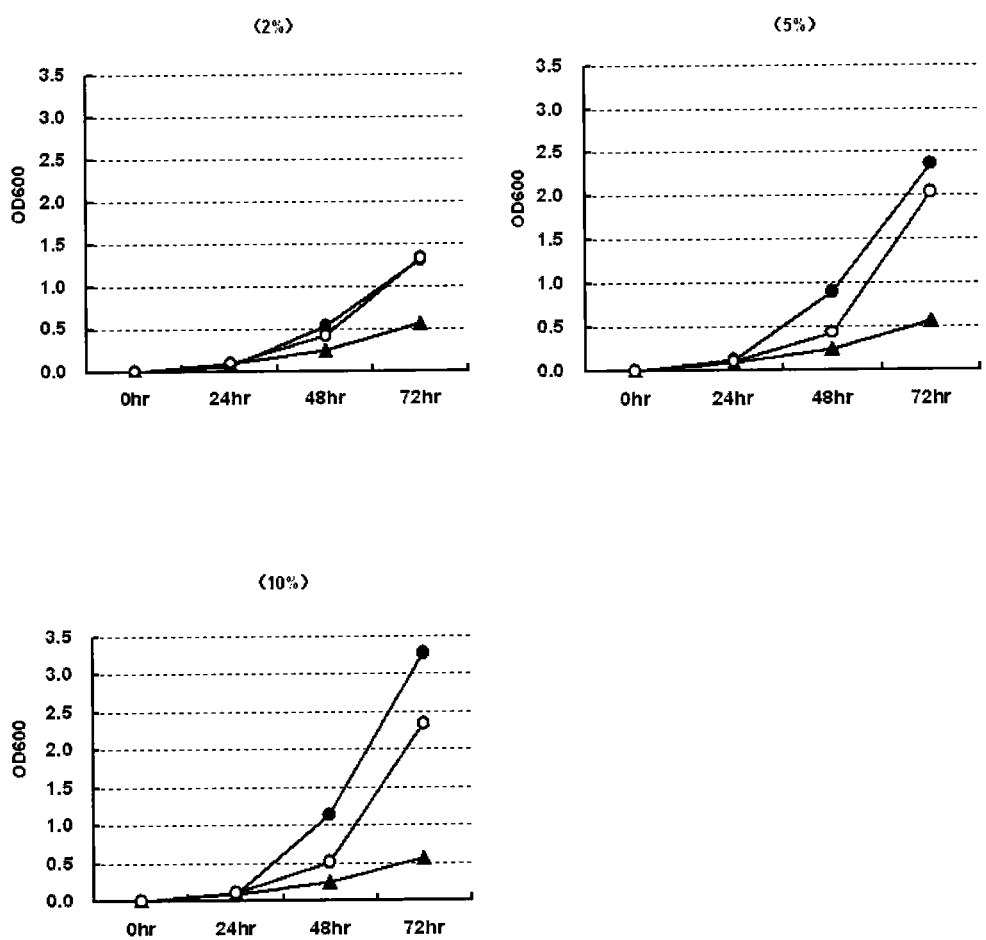
FIG. 1 represents the effect of adding a whey medium culture of the *L. gasseri* OLL2716 strain for the proliferation of propionic acid bacteria, in which a sample containing only GAM bouillon (solid triangle) was used as a control, and compared with a sample containing GAM bouillon plus a whey medium (blank circle), and with a sample containing GAM bouillon plus a whey medium culture of the *L. gasseri* OLL2716 strain (solid circle). The graphs show the results at three different whey medium concentrations 2%, 5%, and 10% indicated at the top of each graph; the vertical axis, medium turbidity ($OD_{600}$); the horizontal axis, culture time.

The present invention is described below in detail.

The present invention provides a composition for enhancing the proliferation activity of propionic acid bacteria in the rumen for the prevention and treatment of acidosis in ruminants. The main activities of the propionic acid bacteria in the ruminant rumen include:

(1) Conversion of lactic acid into propionic acid for the suppression of acidosis.

(2) Suppression of methane bacteria to reduce the amount of methane production (reduce the environmental load).

(3) Promotion of fiber degrading bacteria proliferation to improve energy metabolism.

(4) Resulting improvement of the milk yield and quality.

However, the amounts of propionic acid bacteria present in the ruminant rumen are very unstable, and propionic acid bacteria maybe almost completely absent depending on the type of the feed used. For these and other reasons, the present invention uses viable propionic acid bacteria as a first active ingredient.

The viable propionic acid bacteria used in the present invention are the living bacterium capable of producing propionic acid which are not particularly limited, and preferably belong to *Propionibacterium freudenreichii*. Examples include the ET-3 strain, the ATCC6207 strain, the ATCC8262 strain, the IFO12424 strain, the IFO12426 strain, and the IFO12391 strain of *Propionibacterium freudenreichii*.

The *Propionibacterium freudenreichii* ET-3 strain has been internationally deposited at The National Institute of Advanced Industrial Science and Technology, International Patent Organism Depositary (305-8566, Tsukuba Center, Chuo 6, Higashi 1-1-1, Tsukuba-shi, Ibaraki, Japan) with the accession number FERM BP-8115 (Jul. 11, 2002).

In the present invention, the propionic acid bacteria may be cultured in a medium containing a milk serum (whey and/or whey products treated with protease), and the resulting culture, or the isolated bacteria themselves may be used as the viable propionic acid bacteria.

The propionic acid bacteria may be cultured under aerobic or anaerobic conditions (for example, under applied nitrogen gas pressure; 0.5 kg/cm$^2$) according to an ordinary method using a medium containing whey (5 to 15%). Typically, the propionic acid bacteria are cultured at 20 to 40° C., pH 6 to 8, until the bacteria count reaches 10$^9$ cfu/ml or more. According to the above, culturing the propionic acid producing bacteria in a medium containing whey, thus obtained milk serum fermentation product of the propionic acid bacteria may be used directly, or the isolated bacteria may be used as viable propionic acid bacteria. Further, the product may be used after being freeze dried with an excipient such as powdered skim milk, starch, trehalose, cereals, and sugars.

The present invention also uses a lactic acid bacteria culture as a second active ingredient. As mentioned above, the propionic acid bacteria are very difficult to proliferate (proliferation takes time), particularly in the rumen. Thus, simply adding the viable propionic acid bacteria by oral administration does not facilitate the proliferation of the supplemented propionic acid bacteria and the propionic acid bacteria residing in the rumen, and fails to sufficiently improve the rumen environment. In the present invention, therefore, a lactic acid bacteria culture is used together as a component that promotes proliferation of the propionic acid bacteria.

The lactic acid bacteria culture used in the present invention is not particularly limited, and is preferably a whole lactic acid bacteria culture (including viable bacteria and/or killed bacteria) obtained by culturing lactic acid bacteria (for example, the *Lactobacillus gasseri* OLL 2716 strain) belonging to *Lactobacillus gasseri*. The lactic acid bacteria culture may be at least one selected from bacteria isolated from the culture (viable bacteria and/or killed bacteria), disrupted bacteria (disrupted lactic acid bacteria), a lactic acid bacteria culture residue obtained by removing the solid (including the bacteria) from the culture (includes the culture fluid, and the clear culture supernatant, not the turbid portion of the culture fluid), and products obtained by treating these products. Here, the treated products include at least one of a concentrated product, a paste product, a dried product (at least one of a spray dried product, a freeze dried product, a vacuum dried product, and a drum dried product), a liquid product, a diluted product, and a sterilized product. Further, these components may be used with additional components such as an excipient (such as starch, dextrin, a milk component, and silicic acid), water, a feed component, lactic acid, and lactate.

*L. gasseri* is preferred for use in the present invention, because it has not only strong acid resistance and high acid producing capability, but notably high production efficiency of lactic acid from lactose in a medium containing a whey or other products treated with a protease, as compared with other bacteria such as *L. bulgaricus*.

The *Lactobacillus gasseri* OLL2716 strain has been internationally deposited at The National Institute of Advanced Industrial Science and Technology, International Patent Organism Depositary (305-8566, Tsukuba Center, Chuo 6, Higashi 1-1-1, Tsukuba-shi, Ibaraki, Japan) with the accession number FERM BP-6999 (Jan. 14, 2000).

The lactic acid bacteria may be cultured according to ordinary methods used to culture lactic acid bacteria and other bacteria. The medium may be, for example, defatted milk, powdered skim milk, a whey, or a whey powder. However, it is preferable to use a synthetic medium or a semisynthetic medium that can be easily used for neutralization culturing in which the cells can grow to high concentration in a maintained certain pH range.

The synthetic medium and semisynthetic medium may use at least one of defatted milk, a powdered skim milk, a whey, and a whey powder, or a product obtained by treating these products with a protease. It is also preferable to use a whey protein concentrate (WPC), a whey protein isolate (WPI), or an enzyme treated product of these. In this case, it is desirable to use 1 to 10% lactose in combination. In the neutralization culturing, the lactic acid bacteria are inoculated to the medium, and cultured at 35 to 42° C. in a culture fluid while keeping pH at 4.5 to 7.0 by adding an alkaline solution in amounts that depend on the amounts of the lactic acid to be produced. The lactic acid bacteria are cultured for 24 to 48 hours until the number of bacteria cells in the culture broth reaches $10^9$ to $10^{11}$ cfu/ml, and until the lactic acid content becomes 2.5% or more. The supernatant obtained after centrifuging the culture can then be used.

In the present invention, the viable propionic acid bacteria and the lactic acid bacteria culture are orally administered to a ruminant either simultaneously or separately. For example, for administration to a cow, a viable bacteria material of the propionic acid bacteria ($10^{11}$ cfu/g of the number of the viable bacterial cells) is administered preferably in 0.01 to 10 g/head/day (preferably, 0.1 to 5 g/head/day), and a lactic acid bacteria culture that makes the final acid level (lactic acid content) 0.5 to 6% is administered in 1 to 15% of the viable propionic acid bacteria material, either simultaneously, or immediately before or after the administration of the propionic acid bacteria. For other ruminants, the dose may be increased or decreased according to such factors as the body weight. Note that the composition of the present invention may be administered to a ruminant by being added to, for example, feeds, drinking water, and a milk substitute, instead of being directly administered itself.

The composition according to the present invention may be used as a drug or a feed for ruminants using the viable propionic acid bacteria and the lactic acid bacteria culture as active ingredients. Examples of preparations as ruminant drugs for oral administration include tablets, pills, granules, soft and hard capsule formulations, powders, fine granules, emulsions, suspensions, syrups, elixirs. These preparations may be formulated according to an ordinary method by adding known formulation aids which can be commonly used in the pharmaceutical formulation technical field, such as an excipient, a binder, a disintegrant, a lubricant, a corrigent, a solubilizing agent, a suspension agent, and a coating agent, to the principal agent. When used as a feed and/or a feed additive (agent), the composition may be used as freeze dried product by adding an excipient, for example, such as powdered skim milk, starch, trehalose, cereals, and sugars.

Examples of the ruminants targeted by the present invention include cows, goats, sheep, deer, water buffalo, and camels. Considering use of milk and meat as food in stock farming, it is preferable to use cows, goat, and sheep bred as domestic animals.

As described above, administering the composition according to the present invention to a ruminant promotes the proliferation of the propionic acid bacteria (and the administered viable propionic acid bacteria) in the ruminant rumen, and can thus effectively prevent and treat rumen acidosis.

Typically, the lactic acid content in rumen liquor fluctuates over a wide range from 3 to 130 mg/100 ml, and it is not necessarily the case that the lactic acid is always present in amounts that the propionic acid bacteria can effectively make use of. In these cases, it is difficult to constantly proliferate and exploit the capability of both the propionic acid bacteria indigenous to the rumen, and the propionic acid bacteria supplemented. The lactic acid bacteria culture containing materials such as lactic acid, lactose, and nitrogen compounds is thus used together to provide the proliferation promoting effect for both the indigenous and the administered propionic acid bacteria.

Note that the composition including the viable propionic acid bacteria and the lactic acid bacteria culture of the present invention as active ingredients may also be administered to animals other than ruminants. For example, the invention is also applicable to domestic animals such as chickens, pigs, sheep, and horses; poultries; rodents such as mice, rats, guinea pigs, hamsters, and ferrets; small pet animals such as dogs and cats; animals housed at the zoo (pets or caged animals); and humans and other mammals. The composition according to the present invention also can be administered to these animals to improve their enteral environment.

Examples of the present invention are described below. Note, however, that the present invention is not just limited to the following Examples.

Example 1

It has been indicated that the *L. gasseri* OLL2716 strain has a much higher proliferation ability under low pH conditions than other bacterial strains such as *L. acidophilus, L. rhamnpsus, L. salivarius*, and *L. brevis*. Thus, the following tests were conducted to measure and compare the proliferation ability and the lactic acid producibility of different strains of *L. gasseri*. Nine kinds of *L. gasseri* (Tables 1 and 2) were actively cultured twice in MRS Broth (DIFCO) at 37° C. for 18 hours, and aerobically cultured at 37° C. after being inoculated in a 10 μl-MRS Broth brought to pH 4.0. After 9 hours from the start of culturing, the medium turbidity ($OD_{650}$) and the lactic acid concentration (g/l) in the medium were measured.

Table 1 represents the proliferation ability of *L. gasseri* under low pH conditions. Among the different bacterial strains, the *L. gasseri* OLL2716 strain showed the highest turbidity of 0.248. Table 2 represents the lactic acid producibility of the *L. gasseri* under low pH conditions. The lactic acid concentration after 9 hours of culturing was the highest in the *L. gasseri* OLL2716 strain (5.57 g/l).

TABLE 1

| Bacterial strain | | $OD_{650}$ after 9 hours of culturing |
|---|---|---|
| Lactobacillus gasseri | OLL2716 | 0.248 |
| Lactobacillus gasseri | JCM1131 (Type strain) | 0.144 |
| Lactobacillus gasseri | JCM1130 | 0.070 |
| Lactobacillus gasseri | Control strain A | 0.105 |
| Lactobacillus gasseri | Control strain B | 0.051 |
| Lactobacillus gasseri | Control strain C | 0.194 |
| Lactobacillus gasseri | Control strain D | 0.082 |
| Lactobacillus gasseri | Control strain E | 0.059 |
| Lactobacillus gasseri | Control strain F | 0.031 |

TABLE 2

| Bacterial strain | | Lactic acid concentration after 9 hours of culturing (g/l) |
|---|---|---|
| Lactobacillus gasseri | OLL2716 | 5.57 |
| Lactobacillus gasseri | JCM1131 (Type strain) | 3.23 |
| Lactobacillus gasseri | JCM1130 | 1.57 |
| Lactobacillus gasseri | Control strain A | 2.36 |
| Lactobacillus gasseri | Control strain B | 1.15 |
| Lactobacillus gasseri | Control strain C | 4.36 |
| Lactobacillus gasseri | Control strain D | 1.84 |
| Lactobacillus gasseri | Control strain E | 1.33 |
| Lactobacillus gasseri | Control strain F | 0.70 |

The foregoing results showed that the *L. gasseri* OLL2716 strain has excellent proliferation ability particularly under low pH conditions. The *L. gasseri* OLL2716 strain was therefore found to be most suited for use in the present invention.

Example 2

Promoting effects of adding a whey medium and a whey medium culture for the proliferation of the *Propionibacterium freudenreichii* ET-3 strain were compared, using a whey medium-added GAM bouillon, and a *L. gasseri* OLL2716 strain whey medium culture-added GAM bouillon (Nissui Pharmaceutical Co., Ltd.). The latter is GAM bouillon added with the medium which is obtained by culturing the *L. gasseri* OLL2716 strain in the whey medium.

The *P. freudenreichii* ET-3 strain was subcultured three times in GAM bouillon. Then, samples were prepared that contained only GAM bouillon, GAM bouillon plus a 2%, 5%, or 10% whey medium culture of the *L. gasseri* OLL2716 strain, and GAM bouillon plus a 2%, 5%, or 10% whey medium. The *P. freudenreichii* ET-3 strain ($5.0 \times 10^6$ cfu) was then inoculated to 3 ml of each sample. The proliferation activity (turbidity at $OD_{600}$) under 37° C. anaerobic culture conditions was then measured after 24, 48, and 72 hours of culturing.

While there was no difference between the test groups after 24 hours of culturing, the proliferation activity was clearly enhanced in the *L. gasseri* OLL2716 strain whey medium culture-added group, and in the whey medium-added group after 48 hours and 72 hours of culturing (FIG. 1). The proliferation activity was higher in the *L. gasseri* OLL2716 strain whey medium culture than in the whey medium, and increased volume dependently as the added amounts increased to 5% and 10%. (FIG. 1; presumably because of the combined action of the lactic acid, nitrogen compounds, and other products produced by lactic acid fermentation). These results demonstrated that the whey medium culture of the *L. gasseri* OLL2716 strain has the proliferation promoting effect for the *P. freudenreichii* ET-3 strain, and that the proliferation promoting effect increases in a manner that depends on the added amounts of the whey medium culture of the *L. gasseri* OLL2716 strain.

Example 3

The effects of adding and not adding the *L. gasseri* OLL2716 strain whey medium culture in a rumen was examined using the artificial rumen technique.

Artificial rumen experiments (batch method) were conducted to test the effect of adding the propionic acid bacteria and the *L. gasseri* OLL2716 strain whey medium culture with regard to fermentability associated with propionic acid bacteria proliferation. A 1:2 mixture (15 ml) of the rumen filtrate collected with an oral catheter and synthetic saliva, a hay powder (100 mg), and a blended feed powder (200 mg) were charged into a 50-ml vial, and the *P. freudenreichii* ET-3 strain ($10^7$ cfu) and the *L. gasseri* OLL2716 strain whey medium culture (0.5 ml) were added using a batch method under anaerobic conditions created by $CO_2$ aeration. Fermentability in the rumen was then observed after 6, 12, and 24 hours of culturing.

Figure 2:
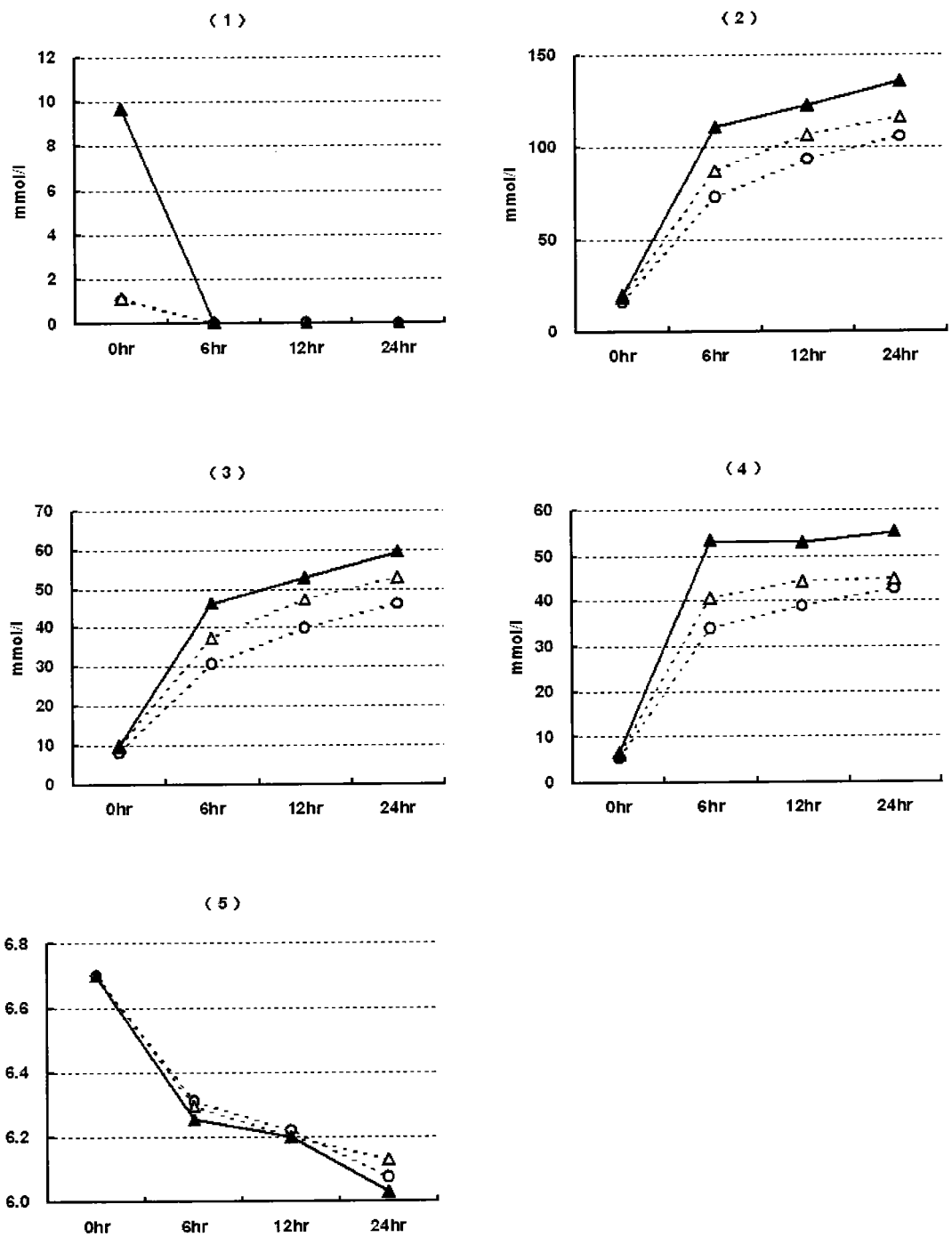
FIG. 2 represents the effect of adding and not adding a whey medium culture of the *L. gasseri* OLL2716 strain in an artificial rumen (in vitro test). The lactic acid concentration (1), total VFA concentration (2), acetic acid concentration (3), propionic acid concentration (4), and pH changes (5) in the artificial rumen after 6, 12, and 24 hours of culturing are presented for three groups: control (blank circle); a *P. freudenreichii* ET-3 strain milk serum fermentation product (containing viable bacteria)-added group (with addition of a *L. gasseri* OLL2716 strain whey medium culture; solid triangle); and a *P. freudenreichii* ET-3 strain milk serum fermentation product (containing viable bacteria)-added group (without addition of a *L. gasseri* OLL2716 strain whey medium culture; blank triangle). In the graphs, the vertical axis represents the concentration of each component (mmol/L) in the artificial rumen ((1) to (4)), and pH value (5). The horizontal axis represents culture time.

The results are presented in FIG. 2. The addition of the *P. freudenreichii* ET-3 strain increased the production of total VFA, acetic acid, and propionic acid after 6, 12, and 24 hours of culturing. Further, the addition of the *L. gasseri* OLL2716 strain whey medium culture further increased the production of total VFA, acetic acid, and propionic acid after 6, 12, and 24 hours of culturing. These results demonstrated that the addition of the *P. freudenreichii* ET-3 strain and the *L. gasseri* OLL2716 strain whey medium culture activates the rumen fermentation by the propionic acid bacteria.

The present invention can be summarized as follows.

The present invention provides a composition that enhances the proliferation activity of propionic acid bacteria in the rumen of ruminants to allow the propionic acid bacteria to sufficiently exhibit their metabolic function in the rumen for the prevention and treatment of rumen acidosis in ruminants. The invention also provides use of the composition. Viable propionic acid bacteria and a lactic acid bacteria culture are orally administered to a ruminant to dramatically (rapidly) promote the proliferation of the propionic acid bacteria in the ruminant rumen, and to thereby increase the volatile fatty acid concentration in the rumen for the prevention and/or treatment of rumen acidosis in the ruminant.

Accession Number

The microorganisms used in the present invention are deposited with the accession numbers below.

(1) *Propionibacterium freudenreichii* ET-3 strain (FERM BP-8115)

(2) *Lactobacillus gasseri* OLL2716 strain (FERN:BP-6999)

The invention claimed is:

1. A method for preventing, treating, or preventing and treating rumen acidosis in a ruminant, the method comprising:
    orally administering a viable propionic acid bacterium and a clear culture supernatant of lactic acid bacteria culture to a ruminant in need thereof and wherein the administering does not include administration of viable lactic acid bacteria, wherein the propionic acid bacterium is the *Propionibacterium freudenreichii* ET-3 strain (FERM BP-8115), and the clear culture supernatant of the lactic acid bacteria is obtained by removing solids from a culture of the *Lactobacillus gasseri* OLL2716 strain (FERM BP-6999).

2. The method of claim 1, wherein the ruminant is a cow.

3. The method of claim 1, wherein the propionic bacterium is administered simultaneously with the clear culture supernatant of the lactic acid bacteria.

4. The method of claim 1, wherein the propionic bacterium is administered immediately before the clear culture supernatant of the lactic acid bacteria.

5. The method of claim 1, wherein the propionic bacterium is administered immediately after the clear culture supernatant of the lactic acid bacteria.

6. The method of claim 1, wherein the propionic bacterium is administered in an amount of 0.01 to 10 g/head/day.

7. The method of claim 1, wherein the propionic bacterium is administered in an amount of 0.1 to 5 g/head/day.

* * * * *